United States Patent

Couch

[19]

[11] Patent Number: 6,003,175
[45] Date of Patent: Dec. 21, 1999

[54] LATERAL DECUBITUS POSITIONING DEVICE WITH A DETACHABLE LIMB SUPPORT

[76] Inventor: Denver Couch, 5728 Imperial Key, Tampa, Fla. 33615

[21] Appl. No.: 09/133,631

[22] Filed: Aug. 13, 1998

[51] Int. Cl.$^6$ .................................................. A47B 13/00
[52] U.S. Cl. ......................... 5/601; 5/624; 5/650; 5/628; 5/81.17; 378/177
[58] Field of Search ................................ 5/601, 612, 621, 5/624, 632, 648, 649, 650, 81.1 R, 81.1 T, 625, 628; 378/177, 178, 179, 180

[56] References Cited

U.S. PATENT DOCUMENTS

| | | | |
|---|---|---|---|
| 979,091 | 12/1910 | Pickart | 5/648 X |
| 4,390,015 | 6/1983 | Clements | 5/650 X |
| 4,615,516 | 10/1986 | Stulberg et al. | 5/650 |
| 4,681,309 | 7/1987 | Lechner | 5/648 X |
| 5,213,062 | 5/1993 | Canady, Jr. | 5/625 X |
| 5,507,050 | 4/1996 | Welner | 5/624 X |
| 5,657,367 | 8/1997 | Couch | 378/177 |

*Primary Examiner*—Terry Lee Melius
*Assistant Examiner*—James M Hewitt
*Attorney, Agent, or Firm*—Pendorf & Cutliff

[57] ABSTRACT

A lateral decubitus positioning device with a detachable limb support including an L-shaped rigid member that has a back portion and a base portion. The back portion of the L-shaped rigid member has a plurality of elongated back slots. The base portion of the L-shaped rigid member has a plurality of base slots. A pad member is sized for positioning onto an interior face of the base portion of the L-shaped rigid member. A ridged J-shaped member that has a cradle portion and a cradle extent is provided. A cradle support has a lateral channel. The cradle support is coupled to the cradle extent of the J-shaped member with an adjustment knob positioned through the lateral channel and the cradle extent. A spacer member is fixedly attached to the cradle support and sized to be positioned within one of the back slots of the L-shaped rigid member. Finally, a locking bar secures the cradle support to the L-shaped rigid member.

9 Claims, 4 Drawing Sheets

LATERAL DECUBITUS POSITIONING DEVICE WITH A DETACHABLE LIMB SUPPORT

BACKGROUND OF THE INVENTION

1. Field of the Invention

The present invention relates to a lateral decubitus positioning device with a detachable limb support and more particularly pertains to a device for supporting and elevating the limb of a patient to facilitate the axiolateral radiographic procedure on a patient positioned on a lateral decubitius positioning device.

2. Description of the Prior Art

The use of a limb support is known in the prior art. More specifically, limb supports heretofore devised and utilized for the purpose of supporting the leg and arms of persons are known to consist basically of familiar, expected and obvious structural configurations, notwithstanding the myriad of designs encompassed by the crowded prior art which have been developed for the fulfillment of countless objectives and requirements.

By way of example, the prior art includes U.S. Pat. No. 5,765,564 to Ewing discloses a limb support assembly for use in supporting the legs of a person to keep the heels of the person suffering from a decubitus condition or burned area on a limb above and out of contact with a bed. The assembly includes an inflatable bladder covered with a soft absorbent sock. The bladder is attached to a bed frame. The device would move the unaffected limb out of the way so as to allow the angle needed to take the X-ray.

U.S. Pat. No. 5,560,577 to Keselman discloses an adjustable limb support system for holding in place the limb of a person during surgery. The adjustable support of Keselman is in combination with a vertically adjustable support. The adjustable support includes a retaining block, a compression block, and a compression head.

U.S. Pat. No. 5,345,629 to Ferrand discloses a system for providing universal support for patients, which is an improvement over U.S. Pat. No. 5,023,967 to Ferrand. While this system supports patients, it is more advanced than is needed for limb support during an X-ray.

U.S. Pat. No. 5,280,783 to Focht, Green and Becker discloses a continuous passive motion device for full extension of an articulable leg. The device includes a pair of linking type assemblies which are joined together to establish a four-bar quadrangular shaped structure. The device, however, is designed to allow movement of the leg between a flexed position and a fully extended position.

U.S. Pat. No. 5,023,967 to Ferrand discloses a system for providing universal support for patients. More specifically the system relates to beds that provide adjustment of the position and support of a person recumbent on the bed.

Lastly, U.S. Pat. No. 4,907,251 to Mork et al. discloses a patient positioning device in a medical panorama X-ray photographing apparatus, for coinciding a subject portion of a patient to be examined with a tomographic zone of X-ray tomographing apparatus. This device is used in X-ray photographing of dental arches.

In many medical procedures, a radiographic procedure is required to determine the underlying damage that may exist. In most instances, the patient is placed on a standard hospital table located in radiology. Conventional hospital beds are designed to meet the needs of the patient, the mattresses may be composed of fluid, sand, air, water, etc. These materials do not make easy the radiologist's job in positioning the patient for taking the X-ray.

In some instances, it is nearly impossible to place and maintain a patient and film cassette on an even plane without the use of another person holding the patient. Recently, there has been an attempt to remedy this problem. One such attempt is U.S. Pat. No. 5,657,367 wherein the applicant discloses a lateral decubitus patient positioning device. This device provides the needed support for the patient during the x-ray procedure. Even with this device there are x-ray procedures that require the limb of the patient to be moved and supported, so a to allow lateral photographing of the patients other body parts. Historically, the support and elevation of the patient's limb, to aid in the x-ray procedure, was accomplished by the using another technician or resting the limb on a piece of the x-ray equipment.

Specifically, in taking a cross-table lateral hip x-ray the procedure involves, elevating the pelvis on a firm pillow or folded sheets enough to center the most prominent point of the greater trochanter to the film. The affected extremity is support at the hip level on sandbags or firm pillows. The knee and hip of the unaffected side are flexed and the extremity position is adjusted so as not to interfere with the projection of the central ray. The unaffected leg is rested on a suitable support or the x-ray tube assembly. In this same instance, the film cassette is placed in the vertical position with its upper border in contact with the lateral surface of the body at or just above the level of the crest of the ilium. The lower border is angled away from the body until the film cassette is exactly parallel with the long axis of the femoral neck of the affected leg. The cassette is supported in position with sandbags or a vertical cassette holder.

Accordingly, there is a need for a device that will elevate, support and immobilize the limb that interferes with the lateral x-ray procedure, and will not cause discomfort or injury to the patient.

In this respect, the lateral decubitus positioning device with a detachable limb support according to the present invention substantially departs from the conventional concepts and designs of the prior art, and in so doing provides an apparatus primarily developed for the purpose of supporting and elevating the limb of a patient to facilitate the axiolateral radiographic procedure on a patient positioned on a lateral decubitius positioning device.

Therefore, it can be appreciated that there exists a continuing need for a new and improved lateral decubitus positioning device with a detachable limb support which can be used for supporting and elevating the limb of a patient to facilitate the axiolateral radiographic procedure on a patient positioned on a lateral decubitius positioning device. In this regard, the present invention substantially fulfills this need.

SUMMARY OF THE INVENTION

Accordingly, a primary objective of the lateral decubitus positioning device with a detachable limb support is to provide a device for supporting and elevating the limb of a patient to facilitate the axiolateral radiographic procedure on a patient positioned on a lateral decubitius positioning device. As such, the general purpose of the present invention, will be described subsequently in greater detail.

To attain this, the present invention essentially comprises a generally L-shaped rigid member. The rigid member has a back portion and a base portion. The back portion and the base portion are interconnected one to another at a right angle. The L-shaped rigid member is sized for supporting a patient therein during the movement and placement of the patient into a decubitus position. In addition, the back portion of the L-shaped rigid member has a plurality of elongated back slots. One of each back slot is symmetrical with another of the back slots. The base portion of the L-shaped rigid member has a plurality of base slots. One of each base slots is symmetrical with another of the base slots.

Included is a generally rectangular pad member. The pad member is sized for positioning onto an interior face of the base portion of the L-shaped rigid member. The pad member has a thickness so as to elevate and support the patient. A ridged J-shaped member is provided. The J-shaped member has a cradle portion and a cradle extent. The cradle extent has an opening.

A cradle support is included and has a lateral channel. The lateral channel is spaced from a first edge of the cradle support. The lateral channel extends about ½ a length of the cradle support. The cradle support is coupled to the cradle extent of the J-shaped member with an adjustment knob that is positioned through the opening of the cradle extent and the lateral channel. A spacer member is fixedly attached to the cradle support in a perpendicular orientation. The spacer is sized to be positioned within one of the back slots of the L-shaped rigid member. A locking bar is rotatably coupled to the spacer with a locking knob. The locking bar secures the cradle support to the L-shaped rigid member for allowing the cradle portion to support a limb of a patient above the base portion of the L-shaped rigid member.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved lateral decubitus positioning device with a detachable limb support which has all the advantages of the prior art limb supports and none of the disadvantages.

Another object of the present invention to provide a new and improved lateral decubitus positioning device with a detachable limb support which may be easily and efficiently manufactured and marketed.

A further object of the present invention to provide a new and improved lateral decubitus positioning device with a detachable limb support, which is of a durable and reliable construction.

An even further object of the present invention is to provide a new and improved lateral decubitus positioning device with a detachable limb support, which is provides comfort to the patient by supporting the patient throughout the radiographic procedure.

Still yet another object of the present invention is to provide a new and improved lateral decubitus positioning device with a detachable limb support, which maintains the patient and film cassette in the proper position and on an even plane during the radiographic procedure.

Another object of the present invention is to supporting and elevating the limb of a patient to facilitate the axiolateral radiographic procedure on a patient positioned on a lateral decubitius positioning device.

A further object of the present invention is to eliminate the need for another person to hold the patient, the patient's limb and/or the film cassette in position during the procedure.

An even further object of the present invention lateral decubitus positioning device with a detachable limb support is to eliminate radiation exposure to extra person(s) since none are needed to assist in the procedure.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

Similar reference characters refer to similar parts throughout the several views of the drawings.

DESCRIPTION OF THE PREFERRED EMBODIMENT

Figure 1:
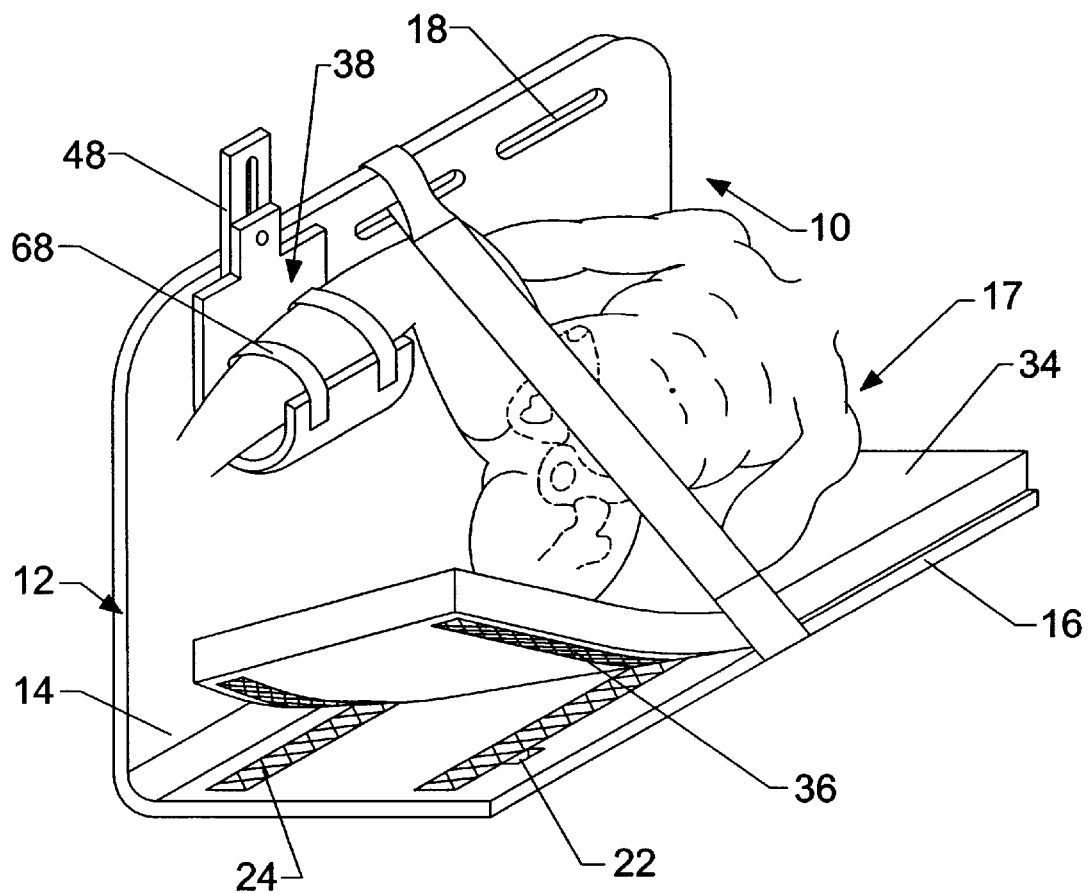
FIG. 1 is a perspective illustration of the preferred embodiment of the lateral decubitus positioning device with a detachable limb support constructed in accordance with the principles of the present invention.

With reference now to the drawings, and in particular to FIG. 1 thereof, a lateral decubitus positioning device with a detachable limb support embodying the principles and concepts of the present invention and generally designated by the reference numeral 10 will be described.

The present invention, the new and improved lateral decubitus positioning device with a detachable limb support, is comprised of a plurality of components. Such components in their broadest context include L-shaped rigid member, a rigid J-shaped member, and a cradle support. Such components are individually configured and correlated with respect to each other so as to attain the desired objective.

More specifically, the present invention includes a generally L-shaped rigid member 12. The L-shaped rigid member is a sheet of rigid plastic having been heated and molded.

Figure 2:
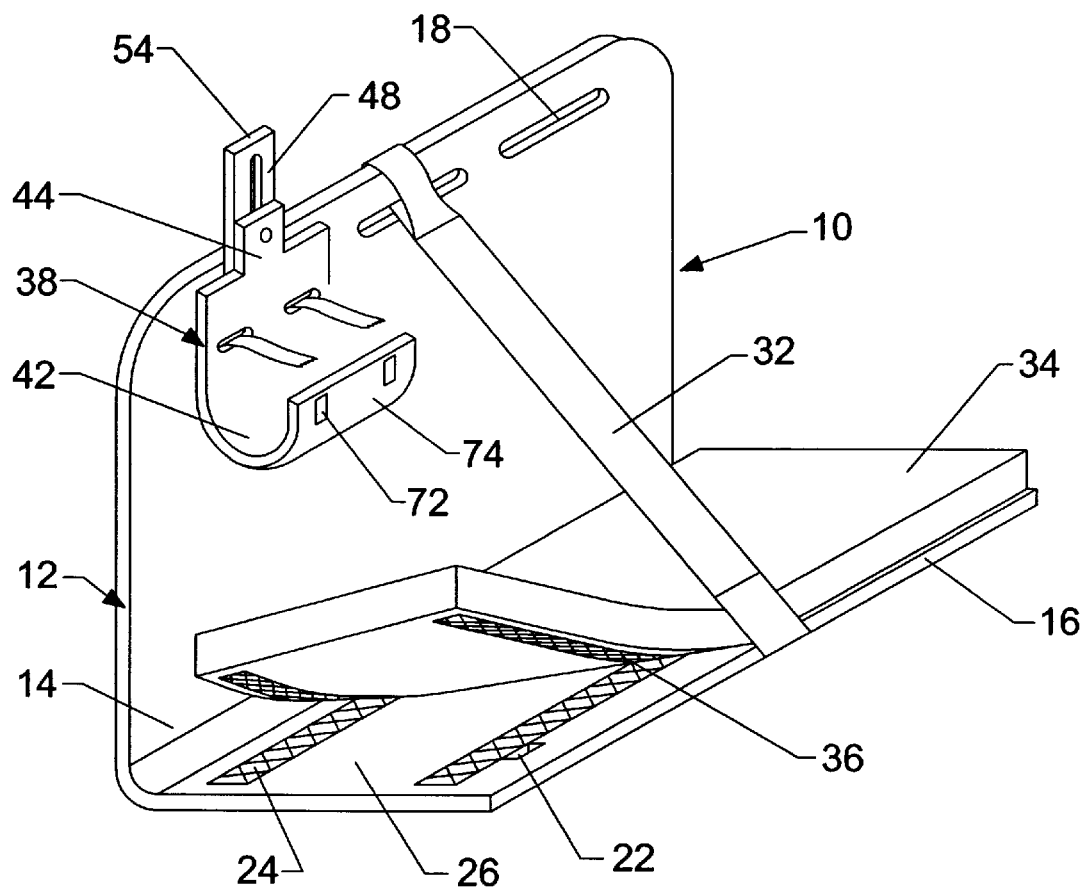
FIG. 2 is an isometric view of the present invention in an operable orientation.

The L-shaped rigid member has a back portion 14 and a base portion 16. The back portion and the base portion are interconnected one to another at a right angle as shown in FIGS. 1 and 2. The L-shaped rigid member is sized to support a patient 17 therein during the movement and placement of the patient into a decubitus position.

Also, the back portion of the L-shaped rigid member has a plurality of elongated back slots 18. One of each back slot is symmetrical with another of the back slots, as shown in FIG. 1. The base portion of the L-shaped rigid member has a plurality of base slots 22, with one such base slot shown in FIG. 2. One of each base slots is symmetrical with another of the base slots. The base portion has a pair of parallel and spaced apart hook and pile-type fastener members 24 along a front face 26 of the base portion.

FIG. 2 shows that there is at least one strap 32 coupled to the L-shaped rigid member. The strap has a first end passed through one of the back slots and another end passed through one of the base slots. The strap is coupled so as to face away from the patient placed within the L-shaped rigid member. The strap is coupled over the patient to secure the patient within the L-shaped rigid member as shown in FIG. 1.

For comfort to the patient, a generally rectangular pad member 34 is included. The pad member is sized for positioning onto the interior face 26 of the base portion of the L-shaped rigid member 12. The pad member has a thickness to elevate and support the patient. The pad member has a pair of parallel and spaced apart hook and pile type fastener members 36. The pair of fastener members are symmetrically positioned for engaging the hook and pile-type fastener members 24 of the base portion.

Figures 3, 4:
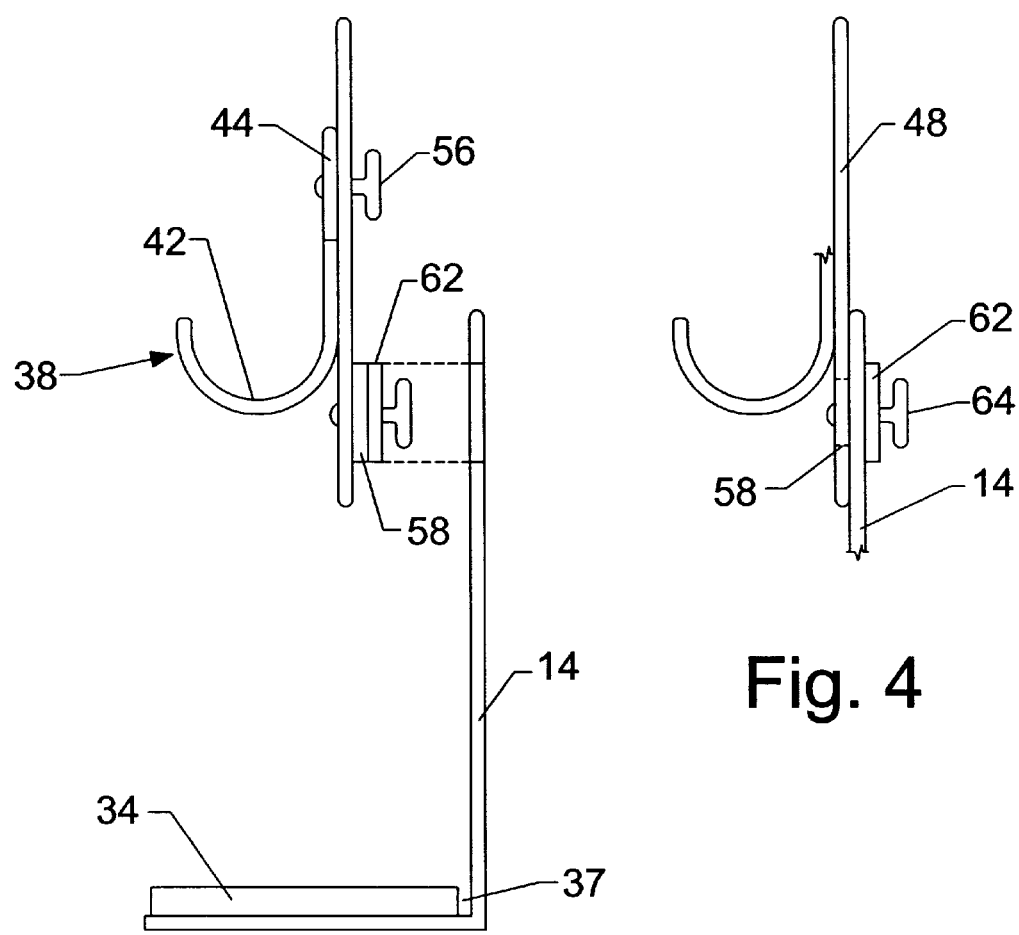
FIG. 3 is a side view of the present invention showing the two main components.
FIG. 4 is a side view of the operable coupling of the present invention.

A film cassette slot 37, as seen in FIG. 3, is formed when the pad is being spaced a certain distance from the back portion of the L-shaped rigid member 12. The distance from the back portion of the L-shaped rigid member is of sufficient size for holding a film cassette parallel to the back portion and a certain distance below the patient.

A rigid J-shaped member 38 is provided. FIG. 2 shows the J-shaped member with a cradle portion 42 and a cradle extent 44. The cradle extent has an opening 46. The cradle portion has a pair of cradle slots 47.

Figure 5:
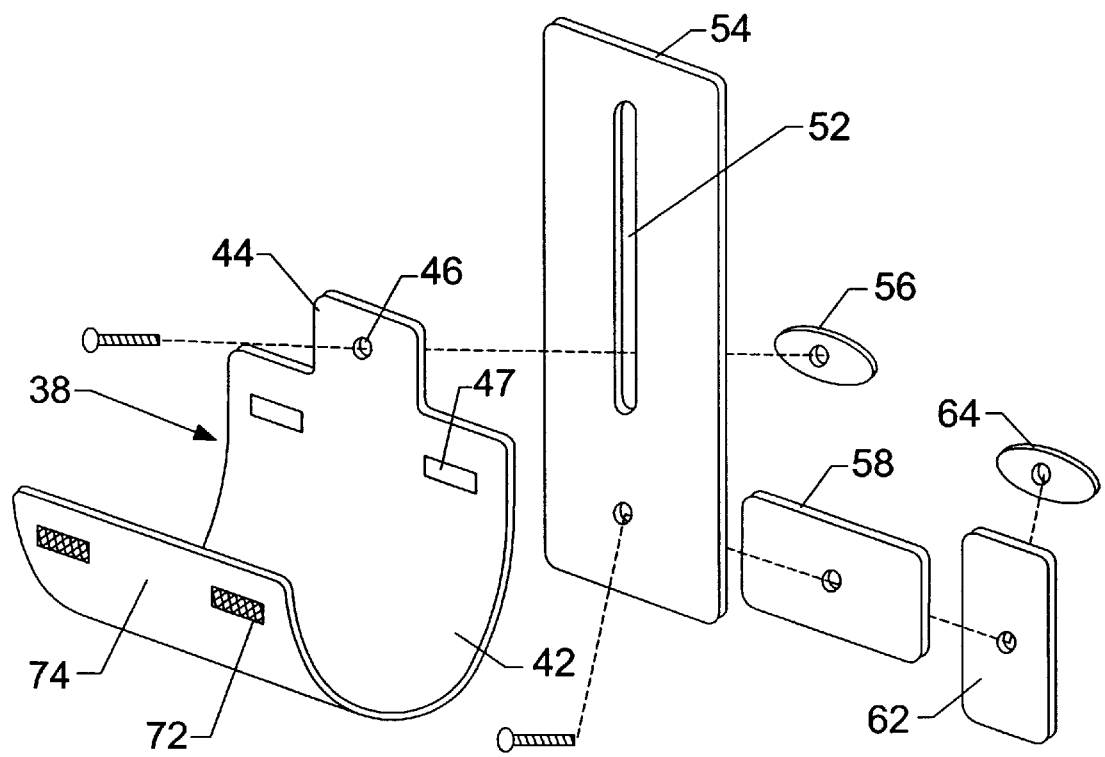
FIG. 5 is an exploded view of the operable components of the limb support of the present invention.

As illustrated in FIG. 5, a cradle support 48 is included. The cradle support has a lateral channel 52. The lateral channel is spaced from a first edge 54 of the cradle support and extends about ½ a length of the cradle support. The cradle support is coupled to the cradle extent 44 of the J-shaped member with an adjustment knob 56 as shown in FIG. 3. The adjustable knob is positioned through the opening of the cradle extent and the lateral channel. The rigid J-shaped member is movable in an upward direction and a downward direction with respect to the cradle support.

A spacer member 58 is fixedly attached to the cradle support 48 in a perpendicular orientation with respect to the cradle support as shown in FIGS. 4 and 5. The spacer member is sized to be positioned within one of the back slots 18 of the L-shaped rigid member. The spacer member holds the cradle support in a vertical orientation with respect to the back portion of the L-shaped rigid member.

Finally, a locking bar 62 is rotatably coupled to the spacer with a locking knob 64. The locking bar, as depicted in FIG. 4, secures the cradle support to the L-shaped rigid member, and allows the cradle portion to support a limb of a patient above the base portion of the L-shaped rigid member. FIG. 1 shows a patient's leg being supported by the cradle.

Furthermore, the J-shaped member is adjustable upwardly and downwardly with respect to the base member when the cradle support is locked in position. Also, at least one cradle strap 68 may be used to secure the patients limb within the cradle. The cradle has at least one section of a hook and pile-type fastener 72 for securing the strap to the under side 74 of the cradle. Once the limb is lifted up and into the cradle, a lateral hip x-ray may be taken of the unaffected limb.

In operation, the patient having an injury to the hip is placed onto the L-shaped rigid member. The patient's decubitus position is arranged for comfort and functionality during the x-ray procedure. Once the patient is secured in the L-shaped rigid member, the unaffected of limb/leg of the patient is lifted and placed in the cradle of the J-shaped member. The height of the cradle is adjusted to afford optimum viewing of the pubis area. Once the patient is in position, the film cassette is slid into the film cassette slot 37 between the pad and the back portion of the L-shaped rigid member.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. It is not intended to be exhaustive or to limit the invention to the precise forms disclosed. Obvious modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, equitably entitled.

What is claimed is:

1. A lateral decubitus patient positioning device with a detachable limb support comprising in combination:

a generally L-shaped rigid member having a back portion and a base portion, the back portion and the base portion being interconnected one to another at a right angle, the L-shaped rigid member being sized for supporting a patient therein during the movement and placement of the patient into a decubitus position;

the back portion of the L-shaped rigid member having a plurality of elongated back slots with one of each of said back slots being symmetrical with another of the back slots;

the base portion of the L-shaped rigid member having a plurality of base slots with one of each of said base slots being symmetrical with another of the base slots;

a generally rectangular pad member being sized for positioning onto an interior face of the base portion of the L-shaped rigid member, the pad member having thickness so as to elevate and support the patient;

a ridged J-shaped member having a cradle portion and a cradle extent; the cradle extent having an opening therethrough;

a cradle support having a lateral channel being spaced from a first edge of the cradle support, the lateral channel extending about one half a length of the cradle support, the cradle support being coupled to the cradle extent of the J-shaped member with an adjustment knob positioned through the opening of the cradle extent and the lateral channel; and a spacer member being fixedly attached to the cradle support in a perpendicular orientation with respect to the cradle support, the spacer being sized to be positioned within one of the back slots of the L-shaped rigid member, a locking bar being rotatably coupled to the spacer with a locking knob, the locking bar securing the cradle support to the L-shaped rigid member for allowing the cradle portion to support a limb of a patient above the base portion of the L-shaped rigid member.

2. A lateral decubitus patient positioning device with a detachable limb support comprising:

a generally L-shaped rigid member having a back portion and a base portion, the back portion of the L-shaped rigid member having a plurality of elongated back slots, the base portion of the L-shaped rigid member having a plurality of base slots;

a pad member being sized for positioning onto an interior face of the base portion of the L-shaped rigid member;

a ridged J-shaped member having a cradle portion and a cradle extent;

a cradle support having a lateral channel, the cradle support being coupled to the cradle extent of the J-shaped member with an adjustment knob positioned through the lateral channel and the cradle extent;

a spacer member being fixedly attached to the cradle support and sized to be positioned within one of the back slots of the L-shaped rigid member; and a locking bar securing the cradle support to the L-shaped rigid member.

3. The lateral decubitus patient positioning device with a detachable limb support as set forth in claim 2, wherein the back portion and the base portion are interconnected to one another at a right angle.

4. The lateral decubitus patient positioning device with a detachable limb support as set forth in claim 3, wherein the L-shaped rigid member is sized for supporting a patient therein during the movement and placement of the patient into a decubitus position.

5. The lateral decubitus patient positioning device with a detachable limb support as set forth in claim 1, including at least one strap wherein the strap is positioned through one of the base slots and one of the back slots, the strap being coupled over the patient to secure the patient within the L-shaped rigid member.

6. The lateral decubitus patient positioning device with a detachable limb support as set forth in claim 2, wherein the cradle extent having an opening therethrough that is in receipt of the adjustment knob when coupled with the cradle support.

7. The lateral decubitus patient positioning device with a detachable limb support as set forth in claim 1, wherein the lateral channel is spaced from a first edge of the cradle support, and the lateral channel extending about one half a length of the cradle support.

8. The lateral decubitus patient positioning device with a detachable limb support as set forth in claim 1, wherein the locking bar is rotatably coupled to the spacer with a locking knob.

9. A lateral decubitus patient positioning device with a detachable limb support comprising:

a generally L-shaped rigid member having a back portion and a base portion, the back portion of the L-shaped rigid member having at least one back slot, the base portion having a pair of parallel and spaced apart hook and pile type fastener members, the L-shaped rigid member being sized for supporting a patient during movement and placement of the patient into a decubitus position;

a pad member being sized for positioning onto an interior face of the base portion of the L-shaped rigid member, the pad member having a pair of parallel and spaced apart hook and pile type fastener members, the pair of fastener members being symmetrically positioned for engaging hook and pile type fastener members of the base portion;

a film cassette slot formed when the pad being spaced a certain distance from the back portion of the L-shaped rigid member, the distance from the back portion being of sufficient size for holding a film cassette parallel to the back portion and a certain distance below the patient;

a ridged J-shaped member having a cradle portion and a cradle extent;

a cradle support having a lateral channel, the cradle support being coupled to the cradle extent of the J-shaped member with an adjustment knob positioned through the lateral channel and the cradle extent;

a spacer member being fixedly attached to the cradle support and sized to be positioned within the back slot of the L-shaped rigid member; and a locking bar securing the cradle support to the L-shaped rigid member for allowing the cradle portion to support a limb of the patient above the base portion of the L-shaped rigid member for the facilitation of an axiolateral radiographic procedure.

* * * * *